United States Patent
Sumanasinghe et al.

(10) Patent No.: US 11,690,705 B2
(45) Date of Patent: Jul. 4, 2023

(54) GRAFT HAVING A POCKET FOR RECEIVING A STENT AND WOVEN GRAFT MATERIAL, FORMING A POCKET

(71) Applicant: Cook Medical Technologies LLC, Bloomington, IN (US)

(72) Inventors: Ruwan Sumanasinghe, Carmel, IN (US); Woong Kim, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 355 days.

(21) Appl. No.: 16/355,163

(22) Filed: Mar. 15, 2019

(65) Prior Publication Data
US 2020/0289253 A1   Sep. 17, 2020

(51) Int. Cl.
*A61F 2/07*   (2013.01)
*D03D 3/02*   (2006.01)
*D03D 11/02*  (2006.01)

(52) U.S. Cl.
CPC .................. *A61F 2/07* (2013.01); *D03D 3/02* (2013.01); *D03D 11/02* (2013.01); *A61F 2002/075* (2013.01); *A61F 2220/0025* (2013.01); *A61F 2230/0023* (2013.01); *D10B 2509/06* (2013.01)

(58) Field of Classification Search
CPC .................. A61F 2/07; A61F 2002/072; A61F 2002/075; A61F 2002/077; A61F 2220/0025; A61F 2230/0023; D03D 11/02; D10B 2509/06
See application file for complete search history.

(56) References Cited

U.S. PATENT DOCUMENTS

| | | | |
|---|---|---|---|
| 6,280,467 B1 | 8/2001 | Leonhardt | |
| 6,475,232 B1 | 11/2002 | Babbs et al. | |
| 6,626,938 B1 | 9/2003 | Butaric et al. | |
| 6,994,724 B2 | 2/2006 | Schmitt | |
| 7,122,052 B2 | 10/2006 | Greenhalgh | |
| 7,226,474 B2 | 6/2007 | Iancea et al. | |
| 7,550,004 B2 | 6/2009 | Bahler et al. | |
| 7,582,110 B2 | 9/2009 | Case et al. | |
| 7,758,626 B2 | 7/2010 | Kim et al. | |
| 8,287,586 B2 | 10/2012 | Schaeffer et al. | |
| 8,696,733 B2 | 4/2014 | Bogert et al. | |
| 9,427,306 B2 | 8/2016 | Shahriari | |
| 9,827,086 B2 | 11/2017 | Winner et al. | |
| 2005/0154446 A1 | 7/2005 | Phillips et al. | |
| 2005/0273155 A1* | 12/2005 | Bahler | A61F 2/07 623/1.13 |
| 2013/0184808 A1 | 7/2013 | Hall et al. | |
| 2017/0105854 A1 | 4/2017 | Treacy et al. | |
| 2018/0202082 A1* | 7/2018 | Van Hulle | D03D 3/02 |

* cited by examiner

*Primary Examiner* — Sarah A Simpson
*Assistant Examiner* — Raihan R Khandker
(74) *Attorney, Agent, or Firm* — Crowell & Moring LLP

(57) ABSTRACT

A tubular graft for use in a stent graft. The tubular graft may include a first woven layer that forms a first side of the tubular graft, where the first woven layer has a set of first warp ends. A second woven layer may forma a second side of the tubular graft, where the second woven layer has a set of second warp ends, and where the second warp ends are distinct from the first warp ends. A woven pocket flap may extend from the first woven layer, where a pocket opening is defined between the woven pocket flap and the first woven layer, and where the woven pocket flap includes at least one common weft yarn with the first woven layer.

14 Claims, 6 Drawing Sheets

GRAFT HAVING A POCKET FOR RECEIVING A STENT AND WOVEN GRAFT MATERIAL, FORMING A POCKET

BACKGROUND

Aneurysms occur in blood vessels in locations where, due to age, disease or genetic predisposition, the blood vessel strength or resiliency is insufficient to enable the blood vessel wall to retain its shape as blood flows therethrough, resulting in a ballooning or stretching of the blood vessel at the limited strength/resiliency location to thereby form an aneurysmal sac. If the aneurysm is left untreated, the blood vessel wall may continue to expand, to the point where the remaining strength of the blood vessel wall is below that necessary to prevent rupture, and the blood vessel will fail at the aneurysm location, often with fatal result.

To prevent rupture, a stent graft of a tubular construction may be introduced into the blood vessel, for example intraluminally. Typically, the stent graft is deployed and secured in a location within the blood vessel such that the stent graft spans the aneurysmal sac. The outer surface of the stent graft, at its opposed ends, is sealed to the interior wall of the blood vessel at a location where the blood vessel wall has not suffered a loss of strength or resiliency. Blood flow in the vessel is thus channeled through the hollow interior of the stent graft, thereby reducing, if not eliminating, any stress on the blood vessel wall at the aneurysmal sac location. Therefore, the risk of rupture of the blood vessel wall at the aneurysmal location is significantly reduced, if not eliminated, and blood can continue to flow through to the downstream blood vessels without interruption.

While tubular stent grafts have been used with success, manufacturing processes remain inefficient and improved connections between the stent and graft body are desired. The present disclosure provides an improved stent graft and method of manufacture that improves the stent-to-graft connection while also increasing manufacturing efficiency relative to prior stent grafts.

BRIEF SUMMARY

In one aspect, the present disclosure describes a tubular graft for use in a stent graft. The tubular graft may include a first woven layer that forms a first side of the tubular graft, where the first woven layer has a set of first warp ends. A second woven layer may forma a second side of the tubular graft, where the second woven layer has a set of second warp ends, and where the second warp ends are distinct from the first warp ends. A woven pocket flap may extend from the first woven layer, where a pocket opening is defined between the woven pocket flap and the first woven layer, and where the woven pocket flap includes at least one common weft yarn with the first woven layer.

In another aspect, the present disclosure describes a stent graft. The stent graft may include a stent and a tubular graft, where the tubular graft includes a first woven layer and a pocket flap extending from the first woven layer. The pocket flap and the first woven layer may include at least one common weft yarn, where a portion of the stent is received by a pocket opening defined between the pocket flap and the first woven layer.

In another aspect, the present disclosure describes a method for forming a tubular graft. The method may include weaving a first woven layer that forms a first side of the tubular graft, the first woven layer having a set of first warp ends, weaving a second woven layer that forms a second side of the tubular graft, the second woven layer having a set of second warp ends, where the second warp ends are distinct from the first warp ends, and weaving a woven pocket flap extending from the first woven layer, where a pocket opening is defined between the woven pocket flap and the first woven layer, and where the woven pocket flap includes at least one common weft yarn with the first woven layer.

BRIEF DESCRIPTION OF THE DRAWINGS

The embodiments will be further described in connection with the attached drawings. It is intended that the drawings included as a part of this specification be illustrative of the exemplary embodiments and should in no way be considered as a limitation on the scope of the present disclosure. Indeed, the present disclosure specifically contemplates other embodiments not illustrated but intended to be included in the claims.

DETAILED DESCRIPTION

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "implantable" refers to an ability of a medical device to be positioned at a location within a body, such as within a body lumen.

As used herein, the term "body vessel" means any tube-shaped body passage lumen that conducts fluid, including but not limited to blood vessels such as those of the human vasculature system, esophageal, intestinal, biliary, urethral and ureteral passages.

The term "branch vessel" refers to a vessel that branches off from a main vessel. The "branch vessels" of the thoracic and abdominal aorta include the celiac, inferior phrenic, superior mesenteric, lumbar, inferior mesenteric, middle sacral, middle suprarenal, renal, internal spermatic, ovarian (in the female), innominate, left carotid, and left subclavian arteries. As another example, the hypogastric artery is a branch vessel to the common iliac, which is a main vessel in this context. Thus, it should be seen that "branch vessel" and "main vessel" are relative terms.

The terms "about" or "substantially" used with reference to a quantity includes variations in the recited quantity that are equivalent to the quantity recited, such as an amount that is insubstantially different from a recited quantity for an intended purpose or function.

The term "stent" means any device or structure that adds rigidity, expansion force, or support to a prosthesis. The term "stent graft" as used herein refers to a prosthesis comprising a stent and a graft material associated therewith that forms a lumen through at least a portion of its length.

Figure 1:
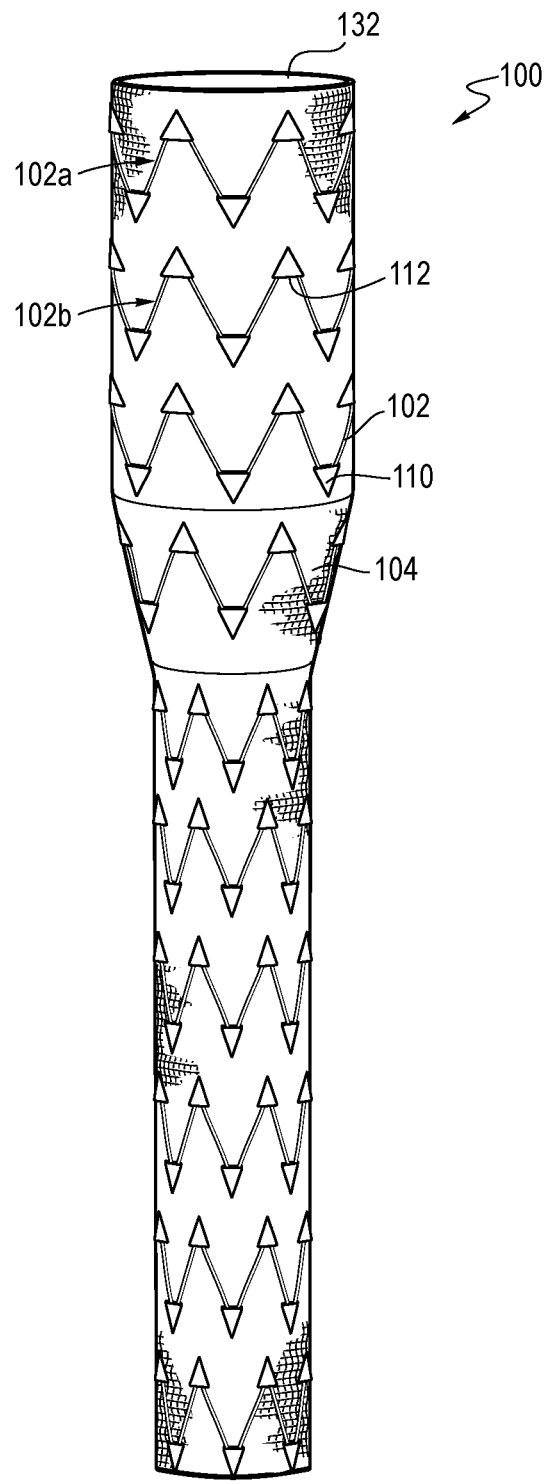
FIG. 1 is an illustration showing a stent graft having a graft body with pockets that receive the stent in accordance with certain aspects of the present disclosure.

FIG. 1 is an illustration showing a top view of a stent graft 100, which may be an implantable stent graft for implantation into a patient body. Without limitation, the stent graft 100 may generally include a stent 102 and a tubular graft body 104 formed of a fabric and/or other suitable graft material (e.g., a woven fabric as described below). The graft body 104 may provide a fluid barrier such that a body fluid can flow through an inner lumen 132 defined by the tubular graft body 104. While the stent 102 may include any suitable support structure, the depicted embodiment of the stent 102 includes several stent sections (e.g., 102a, 102b, etc.) that have several linear segments arranged in a zig-zag pattern. The segments of the stent 102, at least when in an expanded state, provide support to the tubular graft body 104 such that it retains its tubular shape within a patient. While not shown, the stent 102 may also provide anchoring means (e.g., hooks, barbs, or other suitable devices) that anchor the stent graft 100 at an appropriate location within a body lumen when deployed. The stent 102 may be formed with an expandable structure (e.g., self-expanding or expandable upon receipt of an activation force) such that the stent graft 100 can be deployed in a collapsed state and then expanded into an operational state within the body. Optionally, the stent graft 100 may be removable from the body after an amount of time.

As shown, the graft body 104 may include pockets 110 for receiving at least a portion of the stent 102. While the pockets 110 may receive any portion of the stent 102, one exemplary embodiment includes several rows of triangular pockets 110 that receive apices of the respective stent sections 102a, 102b, etc. As shown (and as described in more detail below in FIG. 2), the openings 112 of alternating pockets 110 in each pocket set (e.g., where a set corresponds to a single stent section) may face opposite directions (i.e., distal vs. proximal) to receive respective apices on opposite sides of the sections of the stent 102. As described in more detail below, the pockets 110 may be defined by a two-layer fabric structure having an underlying base layer (e.g., substantially continuous with the areas surrounding the pocket) and a pocket flap, where the space between the base layer and the pocket flap defines a pocket opening. While the pockets 110 are shown as receiving the stent 102 is on the exterior side of the graft body 104, it is contemplated that the stent 102 (and pockets) could instead be located on interior or lumen side of the of the graft body 104.

While the pockets 110 are triangular in the depicted embodiment, they may have any other suitable shape. For example, if the stent 102 includes a different shape (e.g., unsuitable for receipt by a triangular pocket), the pockets 110 can be modified such that they have a shape suitable for receiving such a stent. Without limitation, at least one pocket that accords with the embodiments herein may have a semi-circular or other curved shape, a square shape or shape of another polygon, the shape of an elongated tube, etc.

Further, while the stent graft 100 herein is depicted as having a straight, single-lumen configuration (with multiple diameters), other configurations are also contemplated. For example, the teachings herein also apply to a stent graft that is bifurcated. The formation of pockets on the graft body 104 (as described in more detail below) is not dependent on whether the main body of the graft is straight or whether a straight section is followed by a bifurcated section, and it is contemplated that a bifurcated section may also have pockets appropriately positioned for receipt of one or more stents.

Figure 2:
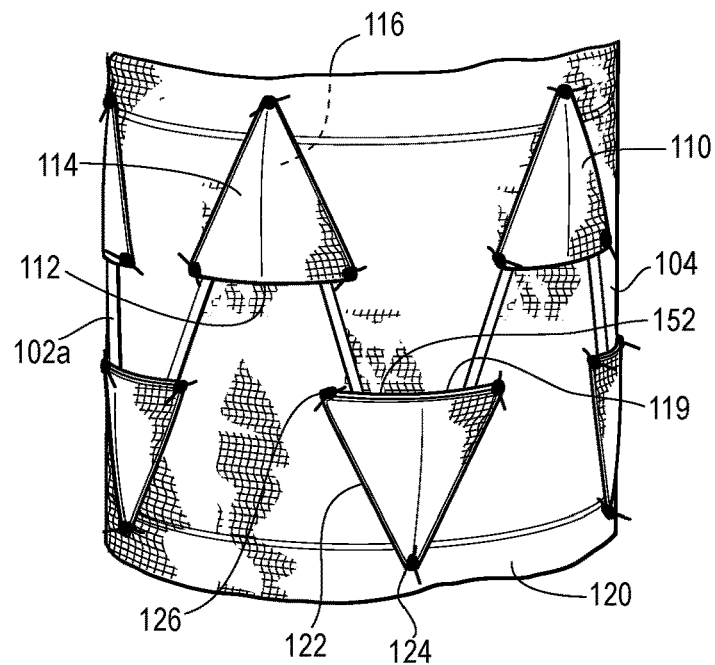
FIG. 2 is an illustration showing a view of a segment of the stent graft shown in FIG. 1, where the pockets are secured an underlying layer of the graft body via tack knots in accordance with certain aspects of the present disclosure.

FIG. 2 shows a magnified view of the stent section 102a along with a set of respective triangular pockets 110. As shown, the opening 112 of the lower pockets 110 face a first direction (e.g., upward from the perspective of FIG. 2) and the openings 112 of the upper pockets 110 face an opposite second direction (downward). The openings 112 are formed between pocket flaps 114 and underlying base layer 116 (beneath the pocket flaps 114 from the perspective of FIG. 2) of the graft body 104, and the openings are accessible through respective mouths 152.

An edge 119 of each of the pocket flaps 114 may be unsecured to the underlying base layer 116 to provide access to the openings 112 (e.g., to allow for receipt of a stent apex) through the mouth 152. Other edges of the pocket flaps 114, such as a second edge 120 and/or a third edge 122, may be at least partially secured to the underlying base layer 116 of the graft body 104 if it is desirable to close those respective sides of the opening 112 off. In other embodiments (particularly when a triangular shape is used for the pockets), only the apices 124 of the pocket flaps 114 may be secured to the remainder of the graft body 104, such as by the tack knots 126 shown in FIG. 2. Securement of the pocket flaps 114 to the remainder of the graft body 104 may be accomplished with any suitable structure or method. For example, the pocket flaps 114 may be secured via a woven or knitted structure (e.g., the woven structures described below), tacks, sewing threads, adhesives, mechanical clamps, etc. While the pocket flaps 114 have generally the same material as the remainder of the graft body 104 in the embodiments described herein (such as a woven material), this is not required.

Figure 3A:
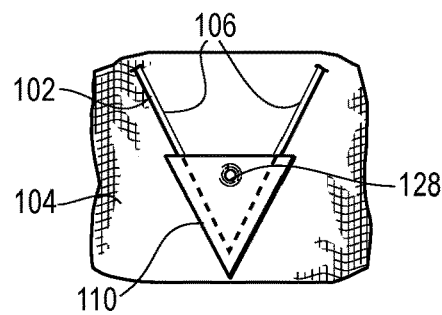
FIGS. 3A-3C are illustrations showing examples of points of securement for locking a portion of a stent within a graft pocket in accordance with certain aspects of the present disclosure.
Figure 3B:
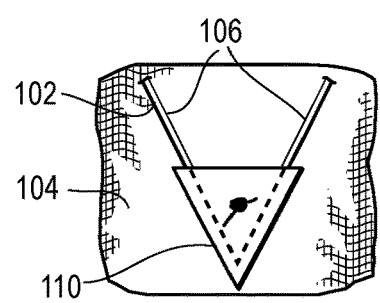
Figure 3C:
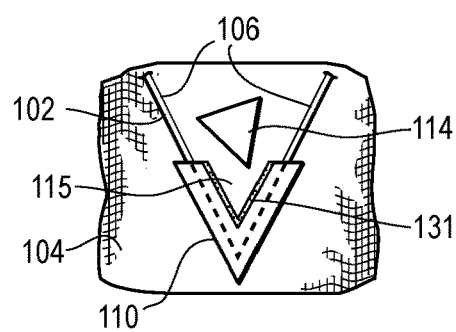

If additional retention of the stent 102 is desirable after its insertion within a pocket opening, additional measures may be taken, some of which are shown in the non-limiting examples of FIGS. 3A-3C. For example, referring to FIG. 3A, the pocket flap 114 may be secured to the underlying base layer 116 at a point of securement 128 after the stent 102 is inserted to lock the stent 102 substantially in place, where the point of securement 128 is spaced from an edge of the pocket flap 114. The point of securement 128, which may be located just inside the apex of the stent 102 and between the two stent sections 106, may be formed via thermally bonding, a sewn knot or other sewn structure, one or more applied adhesives, and/or any other suitable structure or method. For example, FIG. 3B shows a similar point of securement 128 that is formed with a tack knot. In some embodiments (such as that of FIG. 3C), the securement between the pocket flap 114 and the base layer 116 may be more extensive (and intentionally shaped) for enhanced control of the position of the stent 102 relative to the graft body 104. For example, this embodiment includes a v-shaped section 131 formed by thermal bonding (or another securement means) that defines the interior v-shaped dimension of a pocket 110 that mimics the apex of the stent 102. Optionally, non-essential portions of the pocket flap 114 may be removed, and such removal may be advantageous for decreasing the weight of the stent graft, to decrease the area of the graft fabric, to prevent or reduce the likelihood of loose graft material interfering with stent graft deployment and/or body functions, to maintain a low profile of the stent graft device, etc. The features shown in FIGS. 3A-3C and other securement structures may apply to any suitable pocket structure, including the woven pockets described in detail below.

In some embodiments, the material of the graft body 104 may be formed via weaving. Weaving generally involves a set of warp ends (or warp yarns/threads) that are aligned substantially in a first direction, and that are interwoven/interlaced with a plurality of weft yarns aligned substantially in a second direction, where the first direction and the second direction are substantially perpendicular. For example, when a weaving machine is used, the warp ends may be the lengthwise threads attached to a loom before weaving begins, and may be manipulated by a reed during the weaving process. The weft yarns (also known as woof or fill yarns) may be the strands that are shuttled back and forth across the warp ends (while the warp ends are held in an "up" or "down" position by the loom) such that the warp ends and the weft yarns are together interwoven to define a structurally-sound woven fabric. The weaving process may take place on any suitable device (such as a narrow-width shuttle loom) using any suitable yarns materials, yarn types, yarn linear densities, and fabric parameters such as warp density, weft density, and weave design (e.g., plain, twill, rib, etc.).

Figure 4:
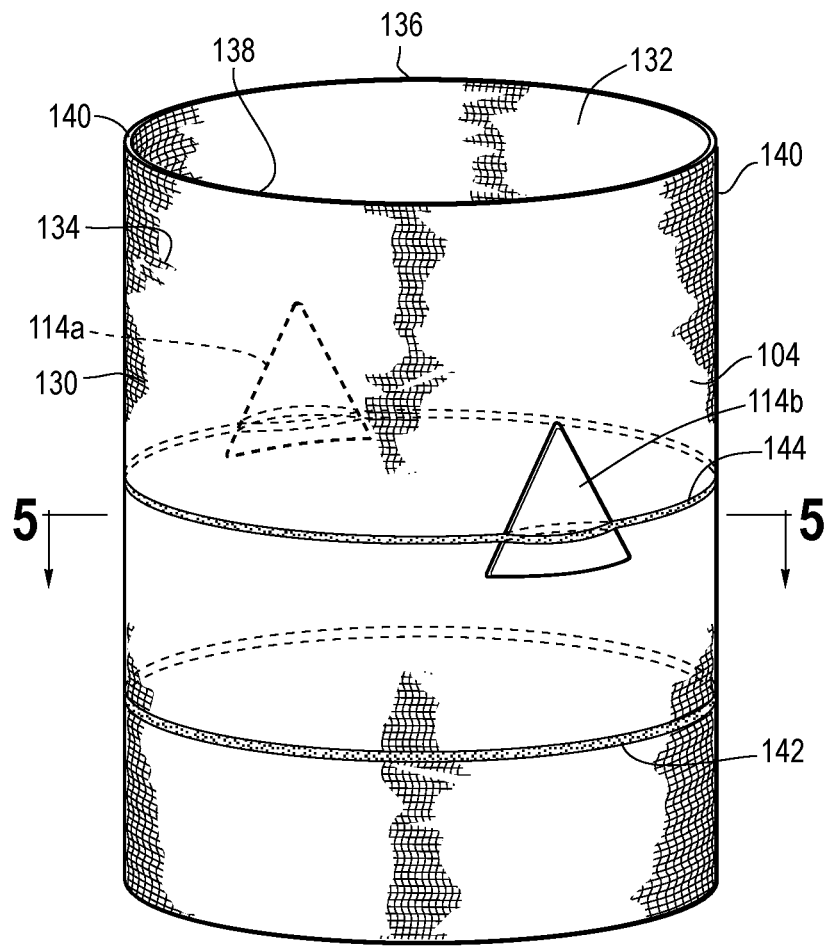
FIG. 4 is an illustration showing a portion of a tubular graft body having woven pockets in accordance with certain aspects of the present disclosure.
Figure 5:
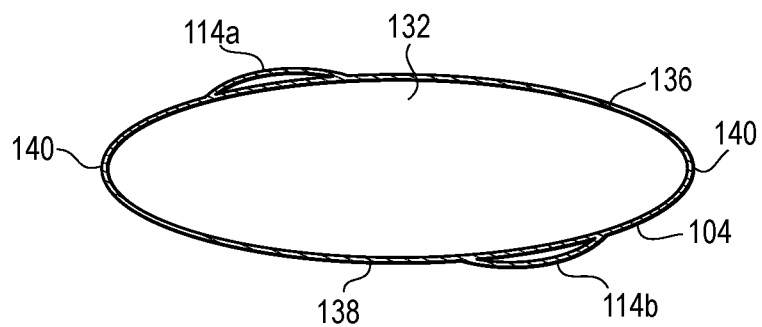
FIG. 5 is an illustration showing a sectional view taken about line 5-5 of FIG. 4.

FIG. 4 shows such an embodiment (with only two pockets for ease of description), where the warp direction (e.g., vertically from the perspective of FIG. 4, and along the lengthwise direction of the warp ends 130 shown in FIGS. 6-9) is parallel to the longitudinal direction of the graft body 104 and its lumen 132. The weft yarns (such as the weft yarns 134 as shown in FIGS. 6-9) within the weave pattern, on the other hand, will generally extend around the circumference of the graft body 104. FIG. 5 shows a sectional view of the woven graft body 104 about line 5-5 in FIG. 4 (except where the graft body 104 is in a flattened state rather than the fully-expanded state of FIG. 4).

Referring to FIGS. 4-5 (and also FIG. 6), the graft material may be woven as a multi-layer fabric. The depicted embodiment includes four layers, but more or fewer layers are also contemplated. Specifically, the depicted embodiment includes a first layer 136 and a second layer 138, where the first layer 136 and the second layer 138 are connected at their edges 140 (but separable between those edges 140). When initially removed from a loom, the first layer 136 and the second layer 138 may be in an overlapping and flat orientation, but once in an expanded state (e.g., with the assistance of a stent), a tubular structure (or other suitable structure with a lumen) may be formed. The lumen 132 may be defined between the first layer 136 and the second layer 138, as shown.

The first layer 136 and the second layer 138 may each form roughly half of the tubular graft body 104, and thus the overall diameter of the lumen 132 may be determined by the size of the first layer 136 and the second layer 138. Thus, the number and/or the density of the of warp ends within the woven layers has a direct impact on the diameter of the graft body 104 (since it determines the width overall width of the layers), for example, and the length of the graft may be determined by a selected length of the warp ends (e.g., which may be cut to such a selected length after weaving is completed on the loom). Other weaving parameters and/or yarn parameters (e.g., warp and weft yarn thickness (linear density), warp density, weft density, and/or weave design) may provide the graft body 104 with certain functional characteristics, such as permeability, longitudinal and circumferential tensile strength, particular fatigue properties, and/or abrasion resistant. Post-processing steps may also impart functional characteristics, such as exposure to other materials, washing, and/or heat-setting to alter the woven dimensions and other characteristics of the material of the graft body 108.

Additional woven layers may define pocket flaps, such as the depicted first pocket flap 114a and second pocket flap 114b. The unique weaving techniques described herein (e.g., with references to FIGS. 6-8) provide an example of a weaving technique for forming such layers integrally with the remainder of the graft body 104. Thus, the pocket flaps 114a and 114b, when formed integrally with the other layers, will have at least one common warp end with the graft body 104 and also at least one common weft yarn. Advantageously, such a structure may have enhanced durability relative to embodiments where the pocket is formed separately and then connected via other means, particularly since the mechanical strength of the connection is not dependent on an external fastening device, and it may avoid potential exposure to other chemicals/materials (such as adhesives) that may deteriorate either the graft body or patient body tissue over a period of time. It may also have enhanced stability in the radial and longitudinal directions. Further, manufacturing efficiency may be improved relative to other woven embodiments since the pockets are formed without significant post-weaving connection steps. Additionally, integral formation of the graft pockets may reduce manufacturing time, reduce undesirable waste, reduce the necessity of adhesives and other materials that may be undesirable for use in a medical device, etc.

Several weavings techniques will now be described for forming different portions of the graft body 104 shown in FIGS. 4-5. Similar and/or identical techniques may be used to form graft bodies with different characteristics (i.e., with additional pockets, pockets having different shapes, etc.). For example, the weaving methods described herein, once understood, can be readily applied to form the graft of FIG.

1 having pockets positioned for receiving a stent. It is noted that the following example sequences are for illustration only, and that certain adjustments and/or changes may be may be made without deviating from the teachings herein.

Figure 6:
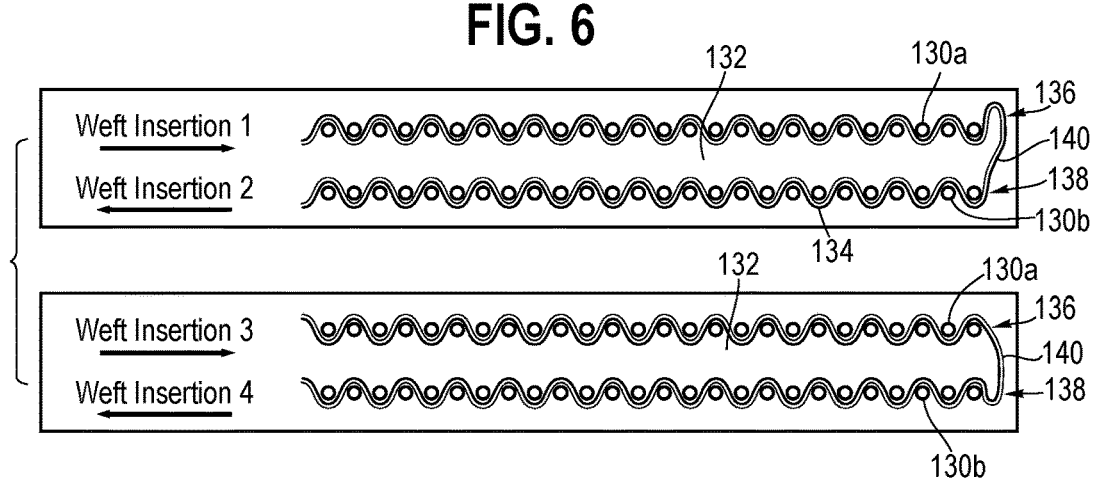
FIG. 6 is an illustration showing a weft insertion sequence for forming a plain tubular fabric for use in a graft body in accordance with certain aspects of the present disclosure.

FIG. 6 shows an example of a weaving sequence (i.e., a weft insertion sequence) for forming plain tubular graft fabric. For example, the sequence of FIG. 6 may form a first area 142 of the graft body 104 as shown in FIG. 4. Referring to FIG. 6, a first set of the warp ends 130 (or "first warp ends 130a") may correspond with the first layer 136 (shown in FIG. 5), and a second set of the warp ends 130 (or "second warp ends 130b") may correspond with the second layer 138 (FIG. 5). To form the tubular structure of the main graft body 104 (FIG. 5), first warp ends 130a may refrain from crossing through the lumen 132 to the second layer 138, and vice versa.

Four weft insertion steps are shown in FIG. 6, which may be repeated as necessary to form a plain tubular fabric of suitable length. In a first weft insertion step (i.e., "weft insertion 1"), the weft yarn 134 is inserted (e.g., via a shuttle portion of a loom as the warp ends are held selectively "up" or "down" via the weaving machine) such that approximately half of the first warp ends 130a are above, and about half are below, the weft yarn 134 (and where all of the second warp ends 130b are below the weft yarn 134). In the second weft insertion step, the weft yarn 134 returns through the fabric in a similar manner, this time such that about half of the second warp ends 130b are above, and about half are below, the weft yarn 134. The third weft insertion step is similar to the first, except the first warp ends 130a switch their position (i.e., "up" vs. "down") relative to the weft yarn 134 to lock a portion of the first layer 136 together and complete one side of the plain tubular structure. Similarly, the fourth weft insertion step is much like the second weft insertion step, except that the second warp ends 130b switch their positions to complete the plain weave structure of the second layer 138.

Notably, while the warp ends 130 extending through the first layer 136 may be distinct from those extending from the second layer 138, the weft yarns 134 may not. That is, a continuous weft yarn 134 may extend through both of the first layer 136 and the second layer 138 such that, when weaving is complete, it extends around the circumference of the graft body. While the weft yarn 134 of FIG. 6 is shown as being continuous on only one side of the weave pattern (e.g., on the right side of FIG. 6), it may also extend from one layer to the other on the other side of the weave pattern. Advantageously, the common weft yarns 134 may secure the first layer 136 to the second layer 138 at the edges 140, completing the tubular structure of the main graft body 104. It is noted that the edges 140 may be substantially undetectable as "edges" once weaving is complete.

Figure 7:
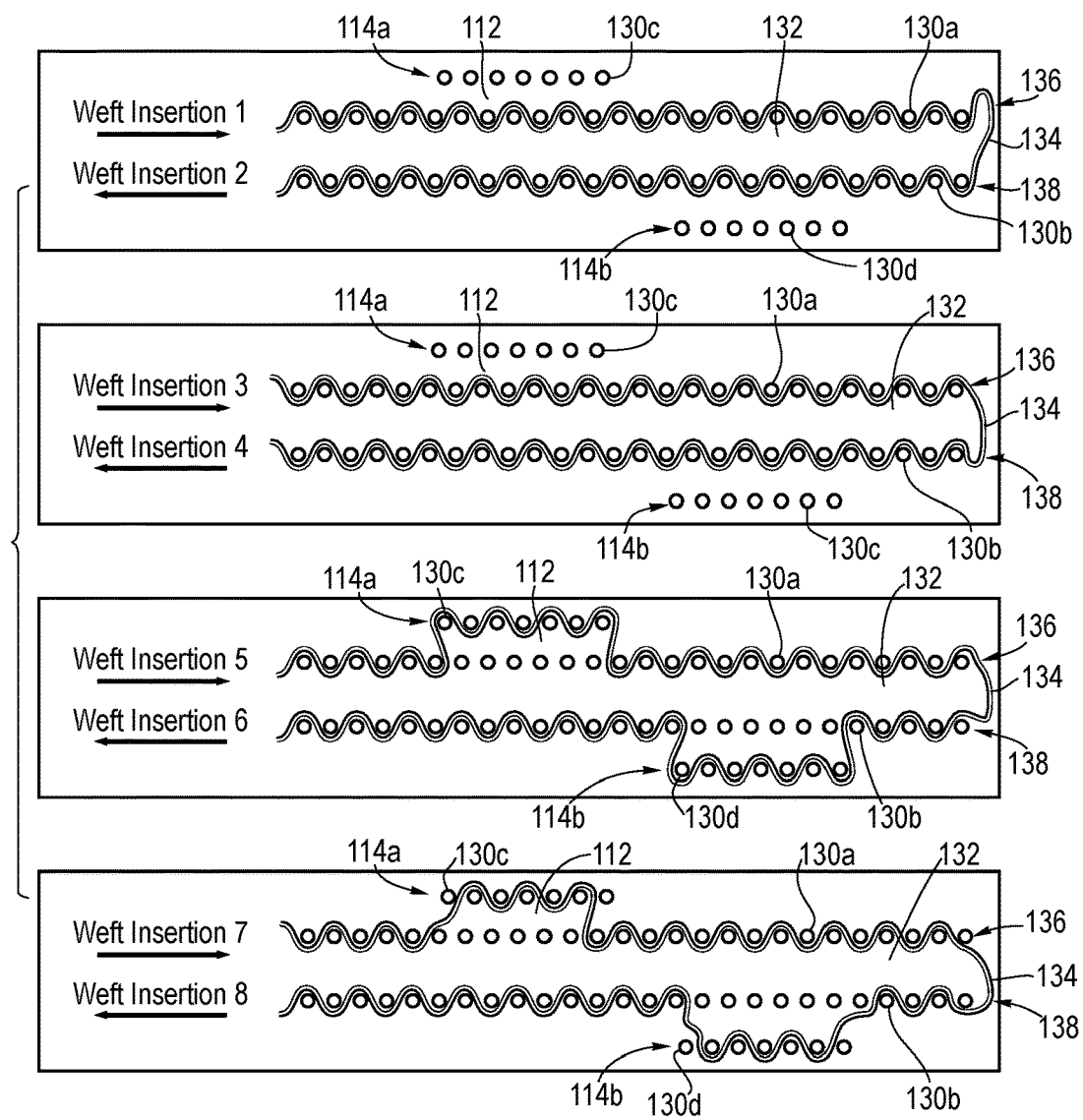
FIG. 7 is an illustration showing a weft insertion sequence for forming a tubular fabric with two pockets for use in a graft body in accordance with certain aspects of the present disclosure.

FIG. 7 shows an example of a weaving sequence (i.e., a weft insertion sequence) for forming a tubular graft fabric having additional layers, such as layers for forming pocket flaps. For example, the sequence of FIG. 7 may form a second area 144 of the graft body 104 as shown in FIG. 4.

Referring to FIG. 7, a first set of the warp ends 130 (or "first warp ends 130a") may correspond with the first layer 136 (shown in FIGS. 4-5), and a second set of the warp ends 130 (or "second warp ends 130b") may correspond with the second layer 138. Like the plain-tubular sequence described above, a set of first warp ends 130a may correspond with a first layer 136 and a second of second warp ends 130b may correspond with a second layer 138. Additional subsets of warp ends may be isolated from the first and second warp ends 130a, 130b for formation of other components. For example, in the depicted embodiment, a set of third warp ends 130c may be associated with the first pocket flap 114a (shown in FIG. 5) and a set of fourth warp ends 130d may be associated with a second pocket flap 114b.

The first four weft insertion steps of FIG. 7 are nearly identical to the four weft insertion steps of FIG. 6, the only difference being the exclusion of the third warp ends 130c and the fourth warp ends 130d from those utilized in the first and second layers 136, 138. Thus, it shall be understood that the first four weft insertion steps will create a small length of tubular woven fabric. Further, it should be noted that the third warp ends 130c and the fourth warp ends 130d are freely floating during these first four weft insertion steps, potentially blocking access to a pocket opening (where "float" is defined herein to mean that a section of a yarn that bypasses other yarns such that it extends without being interlaced/interwoven with another yarn). These floating warp ends are addressed below (with reference to FIG. 10).

In the fifth insertion step, the weft yarn 134 extends into the third warp ends 130c while a section of the first warp ends 130a located immediately below are skipped (such that they are not interlaced with the pocket flap 114a, and thus float for a insignificantly small distance within the fabric, which may not be visible). Similarly, in a sixth weft insertion step, the weft yarn 134 extends into the fourth warp ends 130d and skips a section of the second warp ends 130b located immediately above the fourth warp ends 130d. The seventh and eighth weft insertion steps are respectively similar to the fifth and sixth insertion steps, except warp-end orientations are switched to complete a woven portion of each of the first pocket flap 114a and the second pocket flap 114b (as well as surrounding portions of the first layer 136 and the second layer 138). Since the weft yarn 134 extends directly into the respective first layer 136 or second layer 138 at the sides of the pocket flaps 114a and 114b, the side edges of the pocket flaps 114a and 114b (e.g., sides 120 and 122 shown in FIG. 5) will be directly connected to the remainder of the graft body 104 by virtue of common weft yarn. In other words, a single segment of a weft yarn will extend continuously through a portion of the first layer 136, into the pocket flap 114a, and then back into the first layer 136. The same is true of a segment of the weft yarn and the second pocket flap 114b.

Notably, none of the first warp ends 130a cross through the lumen 132 to the second layer 138, nor do they cross through the opening of the first pocket 110a to the first pocket flap 114a, in any of the eight weft insertion steps of FIG. 7. The same is respectively true of the second warp ends 130b. This ensures formation of the openings 112 of the pockets 110 as well as the lumen 132. These steps may be repeated as necessary to form a pocket of an appropriate size (though it should be recognized that merely repeating FIG. 7 will form a pocket with a constant width).

Figure 8:
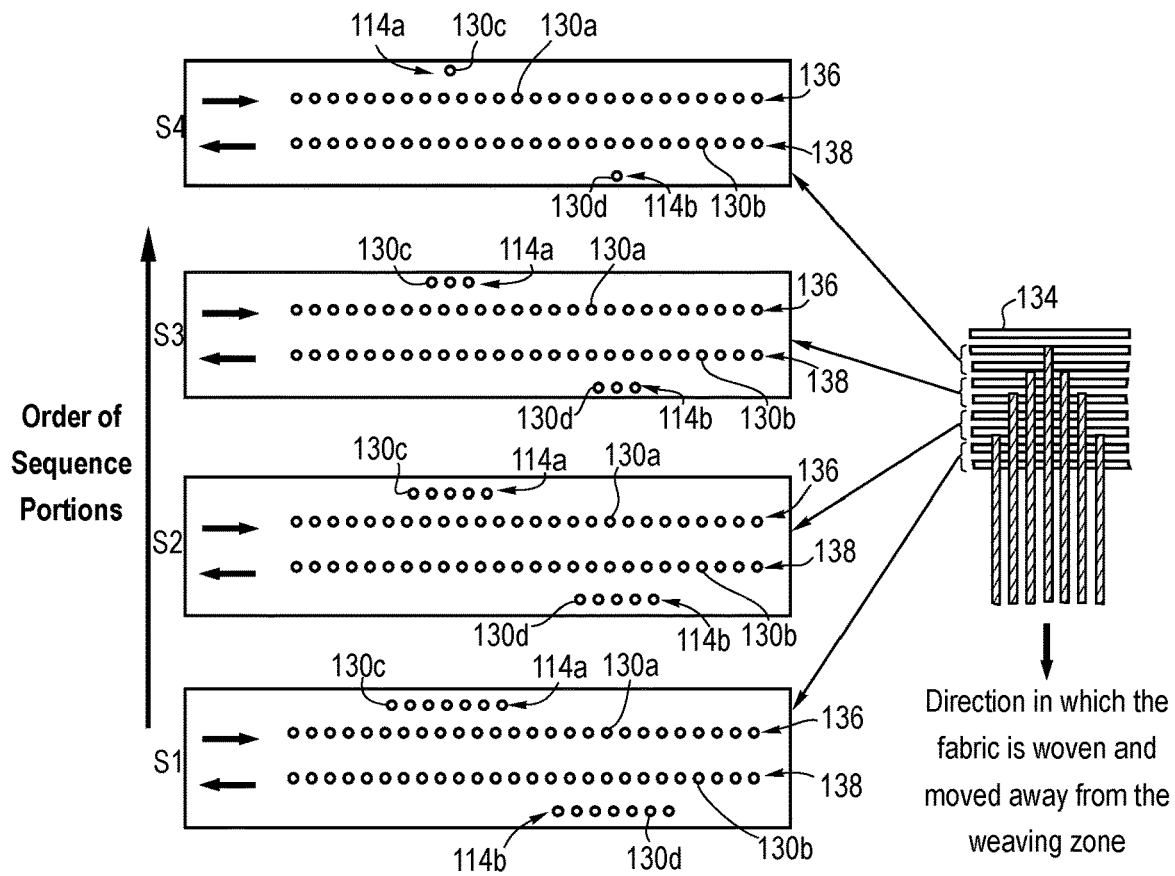
FIG. 8 is an illustration showing a method (including certain steps of four separate weft insertion sequences) for forming a tubular fabric with two pockets having variable width (e.g., such as a triangular pocket) for use in a graft body in accordance with certain aspects of the present disclosure.

FIG. 8 illustrates a weaving method for forming a shaped pocket, such as the triangular pocket 110 of FIG. 4, and it is noted that the specific steps of weft insertion are not included for in the illustration for purposes of concise description. A diagram FIG. 8A generally shows different portions of a pocket that are formed by the sequence portions (S1-S4) depicted by FIG. 8. In short, the sequence portions S1-S4 of FIG. 8 may each follow the teachings of FIG. 7 for forming a pocket extending from a tubular woven fabric, but the number of warp ends used to form the respective pocket flaps 114a and 114b varies moving from one sequence portion to the next.

More specifically, a first sequence portion (or "S1" in FIG. 8), a first pocket flap 114a may be formed with a set warp ends 130c (or "third" warp ends 130c, of which there are seven depicted) and a second pocket flap 114b may be formed with a set of warp ends 130d (or "fourth" warp ends 130d, of which there are seven depicted). As mentioned in the paragraph above, the specific weft insertion steps the sequence portions are not shown here (such as the weft insertion steps where the weft yarn 134 interlaces with the third and fourth warp ends 130c, 130d), and such steps may be similar or identical to those described above with reference to FIG. 7.

After S1 is executed at least once (and notably, it may be repeated), a second sequence portion S2 may be initiated. S2 may involve steps similar to those of S1, but the number of warp ends 130 associated with each pocket flap is different, in this case reduced (here shown as five warp ends, respectively, rather than seven). Thus, the area of the pocket flaps 114 formed by S2 will have a smaller width that is smaller than the width formed by S1. S3 and S4 reduce the number of warp ends 130 used in the pocket flaps 114 further (to three and then one, respectively), such that the width of the pocket flaps 114 continues to decline as weaving continues. After S4 is completed, the weaving machine may form pain tubular fabric (as shown in FIG. 6), thus completing and continuing out of the woven pocket structure. While each subsequent sequence portion involves a reduction in warp ends utilized in a pocket flap, the number could also be increased to thereby increase the width of the pocket. In other embodiments, warp ends from one side of a pocket flap could be dropped from one side of that pocket flap, and others could be picked up on the other side, causing the newly-formed portion of the pocket flap to migrate its position. These techniques can be used to form one or more pockets with any suitable shape, position, orientation, etc.

While may shapes are contemplated, the pocket structures resulting from the sequence of FIG. 8 are triangular, with relatively large widths formed at S1, decreasing widths moving to S2 and then S3, and then reaching a triangle vertex at S4. If each of S1-S4 is executed once, the sides of the triangle may be approximately linear, but this is not required. Further, the sequence portions S2-S4 each drop one warp end from both sides of the respective pocket flaps, but more or less warp ends may be dropped (or picked up) at each sequence portion in other embodiments.

Figure 9:
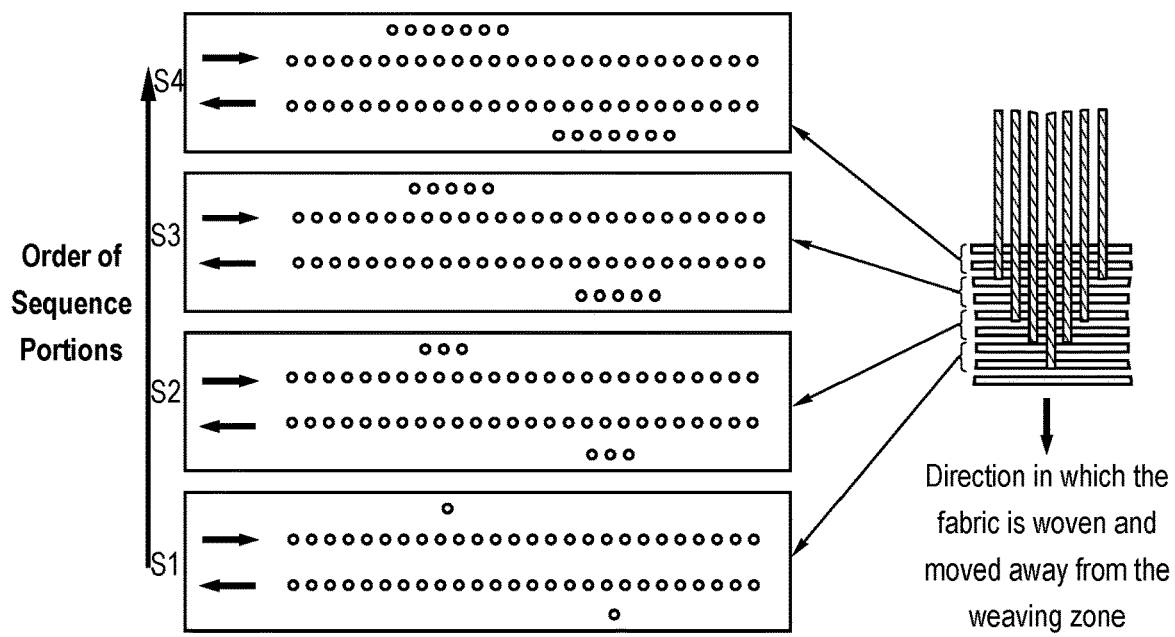
FIG. 9 is an illustration showing a method (including certain steps of four separate weft insertion sequences) for forming a tubular fabric with two pockets having variable width (e.g., such as a triangular pocket) for use in a graft body, where the sequence of FIG. 9 is inverted relative to FIG. 8, in accordance with certain aspects of the present disclosure.

FIG. 9 is similar to FIG. 8, but its steps are inverted for forming an inverted triangle. Only FIG. 8 is described in detail in these paragraphs, but the teachings from FIG. 8 are applicable to FIG. 9 in an inverted fashion.

Figure 10:
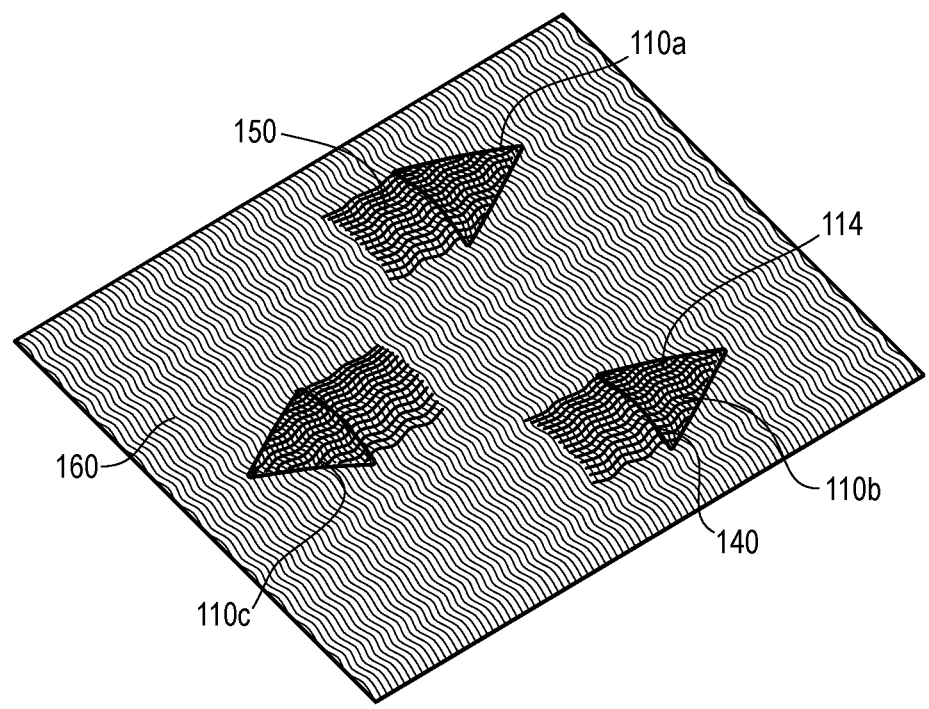
FIG. 10 is an illustration showing a woven fabric having pockets formed in accordance with certain aspects of the present disclosure, where floating warp ends extend from an edge of the pocket.

FIG. 10 shows a portion of woven fabric 160 (e.g., for a graft body or for another application) with triangular pockets 110 formed utilizing the teachings of FIGS. 4-9. For example, two of the pockets 110a-b may be formed utilizing the teachings of FIG. 8, while a third pocket 110c may be inverted (e.g., utilizing a sequence similar to that of FIG. 9), where surrounding areas may be formed utilizing the teachings of FIG. 6. While the woven fabric of FIG. 10 is shown as a flat fabric, it may also be formed as a tubular graft body (as described above) with pockets on each respective side.

Figure 11:
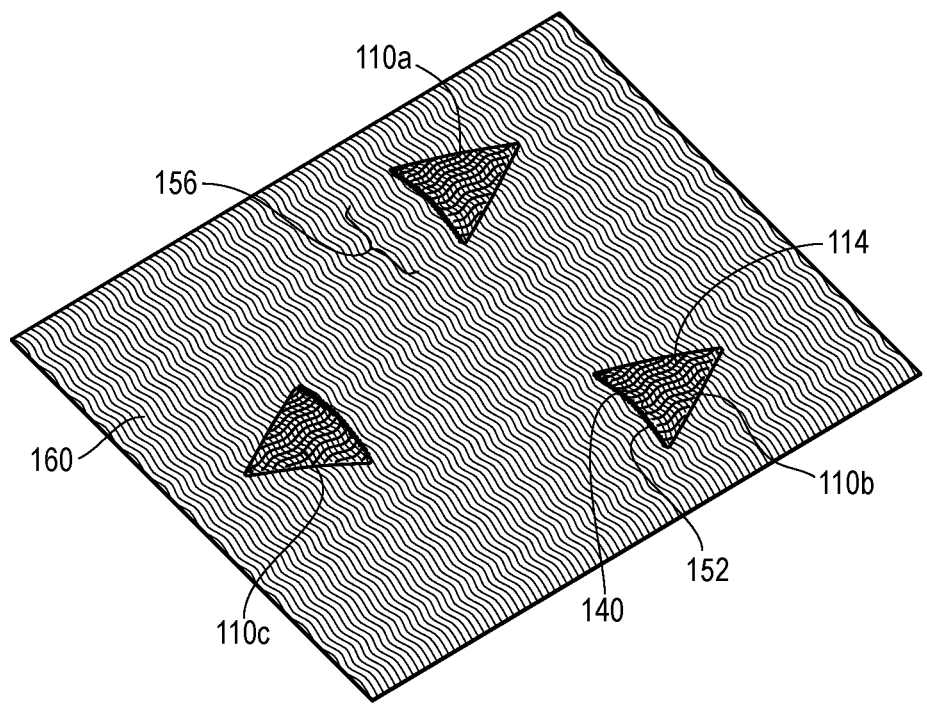
FIG. 11 is an illustration showing the woven fabric of FIG. 10, where the floating warp ends are removed, thereby allowing access to openings of the pockets.

As mentioned briefly above, after the weaving process is complete, access to the pocket openings may be blocked by floating warp ends used at the initiation (or conclusion) of pocket formation. Referring to FIG. 7, for example, the warp ends 114c and 114d may float in the first four weft insertion steps, such that they float over the edge respective pocket flaps 114a and 114b (where the edge is initiated by weft insertion step 5). Thus, a cutting step (or other material removal or material alteration step) may be performed after weaving to provide access to the pocket openings. To illustrate, referring back to FIG. 10, each pocket 110 is associated with a set of floating warp ends 150 that block access to their respective pocket openings. In FIG. 11, these warp ends 150 have been cut away, resulting in pockets 110 with mouths 152 leading to their openings (e.g., for providing access for insertion of stent segments). To ensure the pocket flaps 114 do not unravel at their edges 140 after the cutting procedure, the edges 140 may be heat-processed and/or otherwise treated to finish the edge surface by at least partially securing the severed warp ends together. Optionally, warp ends may also be heat processed or otherwise secured at an area 156 (e.g., at the other end of where the floating warp ends were severed).

While the present invention has been described in terms of preferred embodiments, it will be understood, of course, that the invention is not limited thereto since modifications may be made to those skilled in the art, particularly in light of the foregoing teachings.

We claim:

1. A tubular graft for use in a stent graft, the tubular graft comprising:
    a first woven layer that forms a first side of the tubular graft, the first woven layer having a set of first warp ends;
    a second woven layer that forms a second side of the tubular graft, the second woven layer having a set of second warp ends, wherein the second warp ends are distinct from the first warp ends; and
    a woven pocket flap that extends from the first woven layer, wherein a pocket opening is defined between the woven pocket flap and the first woven layer, and wherein the woven pocket flap includes at least one common weft yarn with the first woven layer,
    wherein the woven pocket flap includes a mouth configured to provide access to the pocket opening, the mouth facing a proximal direction or a distal direction such that the woven pocket flap is configured to receive an apex of a stent through the mouth; and
    the woven pocket flap further comprising a first woven pocket flap and a second woven pocket flap, the mouth further comprising a first mouth facing the proximal direction and a second mouth formed by the second woven pocket flap facing the distal direction for receiving a second apex of the stent.

2. The tubular graft of claim 1, wherein the woven pocket flap includes a triangular shape, wherein a first portion of the triangular shape has more warp ends than a second portion of the triangular shape, and wherein the first portion is adjacent to the pocket opening.

3. The tubular graft of claim 1, wherein the second woven pocket flap extends from the second woven layer, wherein a second pocket opening is defined between the second woven pocket flap and the second woven layer, and wherein the second woven pocket flap includes at least one common weft yarn with the second woven layer.

4. The tubular graft of claim 1, wherein the pocket opening receives a portion of a stent wherein a portion of the stent is located between the first woven pocket flap and the second woven pocket flap when deployed such that the portion of the stent is located radially outside of an outermost surface of the tubular graft.

5. The tubular graft of claim 1, wherein a securement point is formed between the woven pocket flap and the first woven layer to lock a portion of the stent within the pocket opening, and wherein the securement point is spaced from an edge of the woven pocket flap.

6. The tubular graft of claim 1, wherein the mouth for accessing the pocket opening extends radially outwardly from an exterior surface of the tubular graft.

7. A tubular graft for use in a stent graft, the tubular graft comprising:
- a first woven layer that forms a first side of the tubular graft, the first woven layer having a set of first warp ends;
- a second woven layer that forms a second side of the tubular graft, the second woven layer having a set of second warp ends, wherein the second warp ends are distinct from the first warp ends; and
- a woven pocket flap that extends from the first woven layer, wherein a pocket opening is defined between the woven pocket flap and the first woven layer, and wherein the woven pocket flap includes at least one common weft yarn with the first woven layer,
- wherein the woven pocket flap includes a mouth configured to provide access to the pocket opening, the mouth facing a proximal direction or a distal direction such that the woven pocket flap is configured to receive an apex of a stent through the mouth,
- wherein the woven pocket flap includes a set of third warp ends, and wherein within a pocket area, the third warp ends are distinct from the first warp ends and the second warp ends.

8. A tubular graft for use in a stent graft, the tubular graft comprising:
- a first woven layer that forms a first side of the tubular graft, the first woven layer having a set of first warp ends;
- a second woven layer that forms a second side of the tubular graft, the second woven layer having a set of second warp ends, wherein the second warp ends are distinct from the first warp ends; and
- a woven pocket flap that extends from the first woven layer, wherein a pocket opening is defined between the woven pocket flap and the first woven layer, and wherein the woven pocket flap includes at least one common weft yarn with the first woven layer,
- wherein a triangular portion of the woven pocket flap forms an exterior surface of the tubular graft,
- wherein the woven pocket flap includes a mouth configured to provide access to the pocket opening, the mouth facing a proximal direction or a distal direction, and
- wherein the woven pocket flap includes a set of third warp ends, and wherein within a pocket area, the third warp ends are distinct from the first warp ends and the second warp ends.

9. The tubular graft of claim 8, wherein a first end of the triangular portion has more warp ends than a second end of the triangular portion, and wherein the first end is adjacent to the pocket opening.

10. The tubular graft of claim 8, further comprising a second woven pocket flap that extends from the second woven layer, wherein a second pocket opening is defined between the second woven pocket flap and the second woven layer, and wherein the second woven pocket flap includes at least one common weft yarn with the second woven layer.

11. The tubular graft of claim 8, the woven pocket flap further comprising a first woven pocket flap and a second woven pocket flap, wherein the mouth is formed by the first woven pocket flap, and wherein the mouth faces the proximal direction for receiving a first portion of a stent, and wherein a second mouth formed by the second woven pocket flap faces the distal direction for receiving a second portion of the stent.

12. The tubular graft of claim 8, wherein the pocket opening receives a portion of a stent.

13. The tubular graft of claim 12, wherein a securement point is formed between the woven pocket flap and the first woven layer to lock the portion of the stent within the pocket opening, and wherein the securement point is spaced from an edge of the woven pocket flap.

14. The tubular graft of claim 8, wherein the mouth for accessing the pocket opening extends radially outwardly from an exterior surface of the tubular graft.

* * * * *

UNITED STATES PATENT AND TRADEMARK OFFICE
CERTIFICATE OF CORRECTION

PATENT NO. : 11,690,705 B2
APPLICATION NO. : 16/355163
DATED : July 4, 2023
INVENTOR(S) : Ruwan Sumanasinghe and Woong Kim Page 1 of 1

It is certified that error appears in the above-identified patent and that said Letters Patent is hereby corrected as shown below:

On the Title Page

Item (54) and in the Specification, Column 1, Line 3:
Delete "," after MATERIAL and before FORMING A POCKET.

Signed and Sealed this
Twelfth Day of September, 2023

*Katherine Kelly Vidal*

Katherine Kelly Vidal
*Director of the United States Patent and Trademark Office*